United States Patent [19]

Ingraham

[11] Patent Number: 4,634,435
[45] Date of Patent: Jan. 6, 1987

[54] NASO-GASTRIC TUBE

[76] Inventor: Steven A. Ingraham, 5208 Territorial N.W., Albuquerque, N. Mex. 87120

[21] Appl. No.: 768,637

[22] Filed: Aug. 23, 1985

[51] Int. Cl.$^4$ ............................................. A61M 27/00
[52] U.S. Cl. ..................................... 604/268; 264/101
[58] Field of Search .................... 604/101, 45, 96–100, 604/102, 266, 268; 128/207.14, 207.15, 344

[56] References Cited

U.S. PATENT DOCUMENTS

| 4,180,076 | 12/1979 | Betancourt | 604/101 |
| 4,335,719 | 6/1982 | Johnston | 604/97 X |
| 4,341,210 | 7/1982 | Elam | 128/207.15 |
| 4,351,342 | 9/1982 | Wiita et al. | 604/266 X |
| 4,497,318 | 2/1985 | Donmichael | 128/207.15 |

Primary Examiner—Stephen C. Pellegrino
Attorney, Agent, or Firm—Zarley, McKee, Thomte, Voorhees & Seas

[57] ABSTRACT

A naso-gastric tube for removing fluids from a patient's stomach is provided and comprises an elongated tube having a first end and a second end which is adapted for insertion into the patient's stomach. The tube has a plurality of apertures adjacent the second end for providing communication between the patient's stomach and the vent and suction passages of the tube. Cushions or balloons are mounted on the tube adjacent the apertures and are adapted to be inflated so as to protect the apertures from occlusion by the lining of the stomach. The cushions are deflated prior to the tube member being inserted into and removed from the patient's stomach.

9 Claims, 5 Drawing Figures

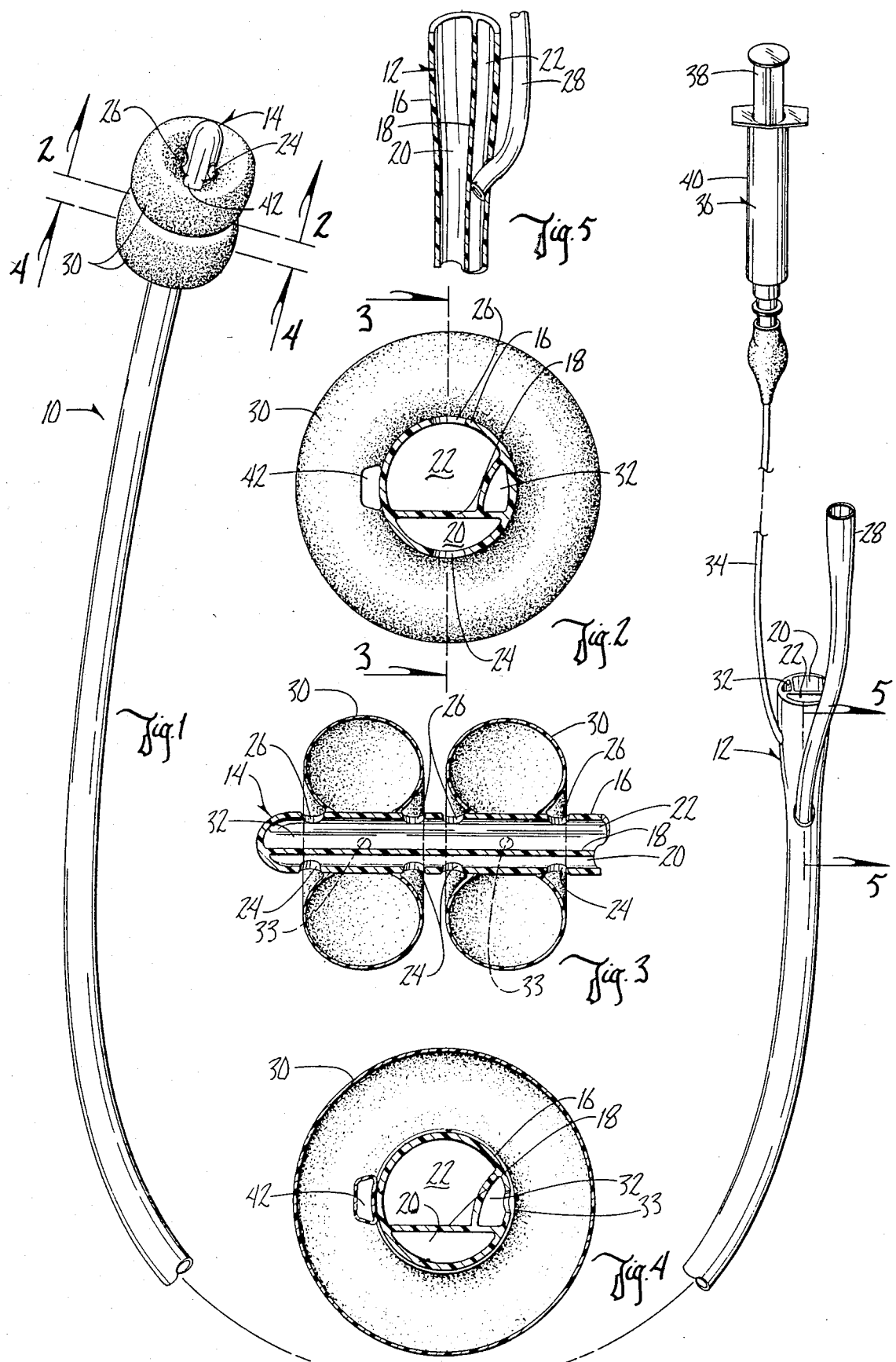

NASO-GASTRIC TUBE

BACKGROUND OF THE INVENTION

Naso-gastric (NG) tubes are used to drain fluid from a patient's stomach. A typical NG tube, called the Salem Sump, used by medical personnel, is both internally and externally vented from the tip and includes a double row of suction ports along one side. The tube is inserted through a patient's nasal cavity until the end of the tube is within the patient's stomach. A suction is then applied to the tube to keep the stomach empty.

Certain problems exist with such conventional NG tubes. Since the lining of the stomach is very soft and pliable and shaped with a series of folds when the stomach is empty, the tube often adheres to the wall of the stomach. In the past, this problem has been overcome by terminating the suction and irrigating the suction ports with saline, and then reapplying the suction. However, the adhesion problem reoccurs frequently such that the irrigation process must be repeated. Also, the adhesion creates a direct pull along the suction ports on the stomach lining which causes bleeding and stress ulcers. Furthermore, the periodic lack of suction allows stomach fluids, including gastric secretions, to accumulate within the stomach, contrary to the purpose of the NG tube. Such build-up of stomach fluids produces patient nausea and emisis. Finally, when the suction ports are not functioning because of adhesion to the stomach wall, the fluids will back up the vent port and be expelled on the bed or floor.

Therefore, a primary objective of the present invention is the provision of an improved naso-gastric tube.

Another objective of the present invention is the provision of an NG tube which removes stomach fluids without adhering to the stomach lining.

A further objective of the present invention is the provision of an NG tube which functions continuously without the need for constant attention by the medical personnel.

Still another objective of the present invention is the provision of an NG tube which is economical to manufacture and safe and durable in use.

SUMMARY OF THE INVENTION

The naso-gastric tube of the present invention utilizes a pair of donut-shaped cushions or balloons secured around the tube adjacent the suction ports such that the ports are not occluded by the stomach lining. The cushions are initially deflated such that the tube can be inserted through a patient's nasal passage and into the stomach. After the end of the tube is in position within the stomach, the cushions are inflated with air. Alternatively, the cushions can be inflated with saline if a weighted tube is desired. The inflated cushions provide a smooth, broad surface to support the stomach lining and to prevent the stomach lining from covering the suction ports. The connection of the cushions to the tube prevents the stomach lining from folding sharply to occlude the suction ports. Thus, blockage of the suction ports is prevented and stress ulcers eliminated.

An opening is provided through the cushions and substantially parallel with the longitudinal axis of the tube such that fluid can flow along the length of the tube. The volume displaced by the cushions is not sufficient to cause the patient to feel nauseated. Also, the diameter of the cushions is sufficiently small to clear the cardiac sphincter and nasal passage without obstructing the airway, should a disoriented patient pull on the tube with the cushion still inflated. Normally, the suction is discontinued and the cushions deflated before removal of the tube from the patient's stomach.

The tube is completely externally vented when viewed by itself, but completely internally vented when viewed with the stomach collapsed around it and serving as the outer perimeter of the suction system. Thus, the stomach lining becomes an integral part of the suction passage structure. There is no internal communication between the suction and vent passages of the tube such that the vent passage does not become occluded by material intended to be removed from the stomach through the suction passage. A vent port is provided for each suction port to further prevent suction of the stomach lining into engagement with the suction port.

BRIEF DESCRIPTION OF THE DRAWINGS

FIG. 1 is a perspective view of the naso-gastric tube of the present invention.

FIG. 2 is a sectional view taken along lines 2—2 of FIG. 1.

FIG. 3 is a sectional view taken along lines 3—3 of FIG. 2.

FIG. 4 is a sectional view taken along lines 4—4 of FIG. 1.

FIG. 5 is a partial sectional view taken along lines 5—5 of FIG. 1.

DETAILED DESCRIPTION OF THE DRAWINGS

The naso-gastric tube of the present invention is generally designated by the reference numeral 10 in the drawings. Tube 10 is elongated and includes an open first end 12 and a closed second end 14. The tube is constructed of an outer wall 16 and an inner wall 18 defining a vent passage 20 and a suction passage 22. Second end 14 of tube 10 includes a plurality of vent ports 24 and a plurality of suction ports 26, both of which extend through outer wall 16 to provide communication between the stomach and vent passage 20 or suction passage 22, respectively. Vent passage 20 is in communication with the atmosphere through a vent line 28 adjacent first end 12, while a suction passage 22 is in communication with a vacuum source (not shown) through a conventional connection at first end 12.

Mounted on tube 10 adjacent second end 14 are a pair of donut-shaped cushions or balloons 30 which are adapted to be inflated and deflated. Cushions 30 are connected to tube 10 adjacent vent ports 24 and suction ports 26 with a relatively sharp angle therebetween, as seen in FIG. 3, so as to prevent the stomach lining from coming into contact with the ports when the tube is in position in the patient's stomach. A small passageway 32 is formed within tube 10 to permit inflation and deflation of the cushions 30. Openings 33 in outer wall 16 of tube 10 provide communication between the interior of cushions 30 and passageway 32. As shown in the drawings, an inflation line 34 provides communication between passageway 32 and an inflation source, such as syringe 36. In order to inflate cushions 30, the syringe plunger 38 is pushed into syringe body 40 and to deflate cushions 30, syringe plunger 38 is retracted from syringe body 40. It is understood that other known means may be employed for inflating and deflating cushions 30, without departing from the scope of the present invention. Also, cushions 30 may be inflated with air, or if a weighted tube is desired or necessary, cushions 30 may be inflated with a liquid such as saline.

An opening 42 is formed within cushions 30 adjacent outer wall 16. Opening 42 is substantially parallel to the longitudinal axis of tube 10 and allows stomach fluids to flow through cushions 30 to suction ports 26.

In operation, cushions 30 are initially deflated so that second end 14 can be inserted through the patient's nasal passage and into the patient's stomach. After second end 14 is in the stomach, cushions 30 are inflated so as to support the stomach lining and so as to prevent the stomach lining from occluding vent ports 24 and suction ports 26. Because the ports are always open, NG tube 10 continually removes fluids from the stomach. Also, since cushions 30 prevent the stomach lining from being sucked into engagement with suction ports 26, stress ulcers are eliminated. Normally, cushions 30 are deflated prior to removal of tube 10 from the patient's stomach. However, cushions 30 are sufficiently small to pass through the cardiac sphincter and the nasal passage without obstructing the airway or injuring the patient should a disoriented patient pull the tube out while the cushions are inflated. Also, the volume displaced by the inflated cushions is not sufficient to cause the patient to feel nauseated.

By itself, tube 10 is completely externally vented. However, when tube 10 is in position in the patient's stomach, the stomach serves as an outer closure of the suction system, such that the system, as a whole, is internally vented. Since there are no openings in inner wall 18, stomach fluid is removed through suction passage 22 without entering or obstructing vent passage 20. As seen in FIG. 3, each suction port 26 has a corresponding vent port 24 to further prevent the stomach lining from being sucked into engagement with the suction ports.

Thus, the improved naso-gastric tube of the present invention operates continuously without discomfort or irritation to the patient and while eliminating or minimizing the time and energy required by the medical personnel to maintain the tube in operating condition. Therefore, the device of the present invention accomplishes at least all of its stated objectives.

What is claimed is:

1. A naso-gastric tube for continuously suctioning fluids from a patient's stomach, comprising:
    an elongated tube member having a first end and a second end, said second end being adapted for insertion into the patient's stomach;
    said tube member including a vent passage for venting the stomach and a suction passage through which fluid can be removed from the stomach, said vent passage and said suction passage being distinct from one another with no direct communication therebetween, said vent passage being in communication with the atmosphere and said suction passage being in communication with a vacuum source;
    said tube member having at least one vent opening adjacent said second end defining an outlet from said vent passage to the stomach and at least one suction opening adjacent said second end defining an inlet from said stomach to said suction passage;
    cushion means on said tube member adjacent said second end of said tube member and adjacent said vent and suction openings and being adapted for inflation so as to protect said openings from occlusion by the lining of the stomach; and
    means for inflating and deflating said cushion means.

2. The naso-gastric tube of claim 1 wherein said cushion means is donut-shaped and extends around said tube member.

3. The naso-gastric tube of claim 1 wherein said cushion means includes an opening extending therethrough substantially parallel with the longitudinal axis of said tube member and adjacent said tube member so as to permit fluid flow through said cushion means.

4. The naso-gastric tube of claim 1 wherein said means for inflating and deflating said cushion means includes a passageway extending along the length of said tube and providing communication between said cushion means and a fluid source.

5. The naso-gastric tube of claim 1 wherein said cushion means is sufficiently small when inflated so as to permit withdrawal of said tube member from the patient's stomach without injuring the patient.

6. The naso-gastric tube of claim 1 wherein said tube member includes a wall separating said vent passage and said suction passage so as to prevent direct communication therebetween.

7. A method for continuously suctioning fluids from a patient's stomach, comprising:
    inserting a naso-gastric tube into the patient's stomach, said tube having a vent passage in communication with the atmosphere through which venting can be provided to the stomach, a suction passage in communication with a vacuum source and through which fluid can be removed from the stomach, at least one vent opening defining an outlet from said vent passage to the stomach, and at least one suction opening defining an inlet from the stomach to said suction passage;
    inflating cushion means on said tube adjacent said vent and suction openings to prevent occlusion of said vent and suction openings by the lining of stomach; and
    continuously applying a vacuum through said suction passage so as to remove fluid from the stomach while simultaneously and continuously providing venting through said vent passage into the stomach.

8. The method of claim 7 futher comprising normally deflating said tube member prior to insertion into and removal from the patient's stomach.

9. The method of claim 7 further including preventing direct communication between said vent passage and suction passage.

* * * * *